US007547761B2

(12) United States Patent
Haines

(10) Patent No.: US 7,547,761 B2
(45) Date of Patent: Jun. 16, 2009

(54) LOW MOLECULAR WEIGHT EXTRACTION PROCESS

(75) Inventor: Stephen Roy Haines, Mosgiel (NZ)

(73) Assignee: Velvet Antler Research New Zealand Limited, Mosgiel (NZ)

( * ) Notice: Subject to any disclaimer, the term of this patent is extended or adjusted under 35 U.S.C. 154(b) by 0 days.

(21) Appl. No.: 10/546,123

(22) PCT Filed: Mar. 19, 2004

(86) PCT No.: PCT/NZ2004/000058

§ 371 (c)(1),
(2), (4) Date: May 22, 2006

(87) PCT Pub. No.: WO2004/083154

PCT Pub. Date: Sep. 30, 2004

(65) Prior Publication Data

US 2006/0241016 A1    Oct. 26, 2006

(30) Foreign Application Priority Data

Mar. 21, 2003    (NZ) .................................. 524868

(51) Int. Cl.
*A61K 38/17* (2006.01)
*A61K 38/18* (2006.01)
*C07K 1/10* (2006.01)
*C07K 14/495* (2006.01)

(52) U.S. Cl. ................... 530/350; 530/399; 530/412; 514/2; 514/8; 514/12; 534/12; 424/85.1

(58) Field of Classification Search ................ None
See application file for complete search history.

(56) References Cited

U.S. PATENT DOCUMENTS

| 3,297,459 | A | * | 1/1967 | Veis et al. ................. 106/157.5 |
| 4,866,033 | A | | 9/1989 | Jaeger |
| 5,147,782 | A | | 9/1992 | Brocks et al. |
| 5,705,477 | A | * | 1/1998 | Sporn et al. ................... 514/2 |
| 6,093,402 | A | | 7/2000 | Miyauchi et al. |

FOREIGN PATENT DOCUMENTS

| JP | 59-118716 A | 7/1984 |
| JP | 2000007697 A | 1/2000 |
| RU | 2112524 C1 | 6/1998 |
| SU | 1822785 A1 | 6/1993 |
| WO | WO 97/00269 | 1/1997 |
| WO | WO 2004/083154 A1 | 9/2004 |

OTHER PUBLICATIONS

Roberts AB, Lamb LC, Newton DL, Sporn MB. De Larco JE, Todaro GJ, Transforming Growth Factors: Isolation of Polypeptides from Virally and Chemically Transformed Cells by Acid?Ethanol Extraction, Proc. Natl. Acaad. Sci, 1980, 77(6):3494-3498.*
Ketterer B, Tipping E, Hackney JF, A Low-Moleuclar-Weight Protein from Rat Liver that Resembes Ligandid in its Binding Properties, Biochm. J., 1976, 155: 511-521.*
NPL-GenBank Accession No. NP_001071296. Accessed Aug. 13, 2008.*
Scopes, Robert K. In *Protein Purification- Principles and Practice*, Third Edition Springer Verlag, 1994, see Sections 4.4 and 4.7.
Supplementary European Search Report for EP 04722118.
Ko et al., "Epidermal Growth Factor From Deer (*Cervus elaphus*) Submaxillary Glad and Velvet Antler" General and Comparative Endocrinology 63, pp. 431-440, 1986.
Weng et al., "A New Polypeptide Promoting Epidermal Cells and Chondrocytes Proliferation From *Cervus elaphus* Linnaeus" Acta Pharmaceutica Sinica , 36(12),pp. 913-916, 2001.
Latest Research http:www.deervelvetinformation.org/research.htm, Apr. 4, 2003 http:www.archive.org/, used to establish the publication date of the document see whole document, pp. 1-12 downloaded on Aug. 26, 2004.
Latest Research http:www.velvita.com/latestresearch.htm, Apr. 7, 2003 http:www.archive.org/, used to establish the publication date of the document see whole document, pp. 1-13 downloaded on Aug. 26, 2004.
Ekstrand A.J. et al. 2003 "Deletion of neuropeptide Y (NPY) 2 receptor in mice results in blockage of NPY-induced angiogenesis and delayed wound healing" *Proc Natl Acad Sci USA* 100:6033-6038.

* cited by examiner

*Primary Examiner*—Cecilia Tsang
*Assistant Examiner*—Julie Ha
(74) *Attorney, Agent, or Firm*—Knobbe Martens Olson & Bear LLP

(57) ABSTRACT

A process for isolating low molecular weight ("LMW") peptides from tissue in situ comprising the steps: a) homogenizing the tissue; b) mixing the homogenized tissue with an organic solvent to form a fully-wetted slurry; c) standing or agitating the slurry to denature the proteins in situ within the tissue; d) removing the organic solvent from the tissue; e) mixing the organic solvent-treated tissue of step d) with a sufficient volume of water or an aqueous solution to extract the peptides; f) separating a liquid extract from the tissue residue of step e) to obtain an aqueous solution containing the low molecular weight peptide fraction removed from the tissue.

16 Claims, 14 Drawing Sheets

Gel filtration chromatography profile of (a) deer velvet total protein extract. (b) deer velvet LMW extract prepared using the new *in situ* extraction process. An approximate molecular weight scale is given below the chromatograms.

A LMW extract prepared by precipitation of high molecular weight proteins from deer velvet total protein extract by addition of cold ethanol in the liquid phase.

Gel filtration chromatography profiles of freeze-dried deer velvet samples extracted with 0.05M phosphate buffer (pH 6.9) following pre-treatment for 3 hours with a 6:1 (v/w) ratio of 30%, 40%, 50%, 60%, 70%, 80% or 90% ethanol, or without pre-treatment (0% ethanol).

A graph showing the effect of pre-treatment of freeze-dried deer velvet samples with 30%, 40%, 50%, 60%, 70%, 80% or 90% ethanol (6:1 v/w), prior to extraction with 0.05M phosphate buffer (pH 6.9), on the total areas of peaks of low and of high molecular weight proteins in the extract solutions.

Gel filtration chromatography profiles of freeze-dried deer velvet samples extracted with 0.05M phosphate buffer (pH 6.9) following pre-treatment for 16.5 hours with a 6:1 (v/w) ratio of 30%, 40%, 50%, 60%, 70%, 80% or 90% ethanol, or without pre-treatment (0% ethanol).

A graph showing the effect of time of incubation used for the pre-treatment of freeze-dried deer velvet samples with 70% ethanol, prior to extraction with 0.05M phosphate buffer (pH 6.9), on the total areas of peaks of low and of high molecular weight proteins in the extract solutions.

A graph showing the effect of the ratio (v/w) of the 70% ethanol used for 3 hour pre-treatment of freeze-dried deer velvet samples, prior to extraction with 0.05M phosphate buffer (pH 6.9), on the total areas of peaks of low and of high molecular weight proteins in the extract solutions.

Gel filtration chromatography profiles of freeze-dried deer velvet samples extracted with 0.05M phosphate buffer (pH 6.9) following pre-treatment for 3 hours with a 6:1 (v/w) ratio of 70% acetonitrile, 70% acetone, 70% propan-2-ol, 70% ethanol or 70% methanol, or without pre-treatment with organic solvent.

Gel filtration chromatography profiles of freeze-dried deer velvet samples extracted with various buffers (each 0.05M) or with 0.05M sodium chloride or water, following pre-treatment for 3 hours with a 6:1 (v/w) ratio of 70% ethanol.

Gel filtration chromatography profiles of freeze-dried deer placenta samples extracted with 0.05M phosphate buffer (pH 6.9) following pre-treatment for 3 hours with a 6:1 (v/w) ratio of 30%, 40%, 50%, 60%, 70%, 80% or 90% ethanol, or without pre-treatment (0% ethanol).

Gel filtration chromatography profiles of freeze-dried deer blood samples extracted with 0.05M phosphate buffer (pH 6.9) following pre-treatment for 3 hours with a 6:1 (v/w) ratio of 30%, 40%, 50%, 60%, 70%, 80% or 90% ethanol, or without pre-treatment (0% ethanol).

Gel filtration chromatography profiles of freeze-dried sheep liver samples extracted with 0.05M phosphate buffer (pH 6.9) following pre-treatment for 3 hours with a 6:1 (v/w) ratio of 30%, 40%, 50%, 60%, 70%, 80% or 90% ethanol, or without pre-treatment (0% ethanol).

Gel filtration chromatography profiles of freeze-dried sheep liver samples extracted with various buffers (each 0.05M) or with water, following pre-treatment for 3 hours with a 6:1 (v/w) ratio of 70% ethanol.

Gel filtration chromatography profiles of frozen and of freeze-dried deer velvet samples extracted with 0.05M phosphate buffer (pH 6.9) following pre-treatment for 3 hours with a 6:1 (v/w) ratio of 70% ethanol, compared to a sample of freeze-dried deer velvet similarly extracted without ethanol pre-treatment.

LOW MOLECULAR WEIGHT EXTRACTION PROCESS

This application is U.S. National Phase of International Application PCT/NZ2004/000058, filed Mar. 19, 2004 designating the U.S., and published in English as WO 2004/083154 on Sep. 30, 2004, which claims priority to New Zealand Patent Application No. 524868 filed Mar. 21, 2003.

TECHNICAL FIELD

The present invention relates to an improved extraction process. In particular, the present invention relates to an improved extraction process for isolating low molecular weight peptides from animal tissue.

BACKGROUND ART

In the health food and biomedical markets there exists a growing demand for extracts of animal products that contain enriched levels of growth factors and other low molecular weight polypeptides. This demand stems from the enhanced bioactivity, and often greater solubility and stability, of the smaller polypeptides relative to the large proteins present in the tissue or other source material. In particular, low molecular weight peptide and growth factor extracts have properties making them suitable for a number of diverse applications including medical (e.g. wound healing) products, ingredients in dietary supplements, cosmetics and cell growth media.

A variety of standard methods for aqueous extraction of animal tissues have been developed and used widely for isolation of proteins, Scopes R.K. (1987). Typically aqueous extraction involves using some method for breaking up cells, such as ultrasound or mechanical disruption (in a blender), in the presence of water or an aqueous salt or buffer. The pH of the extraction system is sometimes manipulated, or detergents and other additives used, in order to enhance the solubility of specific target proteins (e.g. membrane-associated enzymes). However, typically the initial total protein extract will contain proteins having a wide range of molecular weights. Further processing steps are then required for selective enrichment of growth factors and other low molecular weight polypeptides in the total protein extracts.

Commercial production of growth factor-enriched tissue extracts enriched with low molecular weight peptides requires the availability of practical, cost effective methods for removal of unwanted higher molecular weight proteins from the mixtures. Current methods that are applicable on an industrial scale for fractionation of tissue extracts and other animal-derived material (e.g. blood, milk, colostrum), with potential enrichment of growth factors, include:

Ultrafiltration

Gel filtration chromatography (GFC) (also known as size exclusion chromatography)

Other chromatographic fractionation systems (e.g. ion exchange, hydrophobic interaction, affinity)

Liquid phase partitioning in multiphasic systems

Precipitation from aqueous solution (i.e. from the liquid phase) using water miscible organic solvents (ethanol, acetone), typically the organic solvent is ice cold sometimes with the addition of immiscible organic solvents (chloroform) to enhance the denaturing effect, Scopes, R.K. (1987).

Salting out with neutral salts or amino acids

However, in most instances these methods have been used to isolate enzymes and other moderately large proteins, rather than the concentration of growth factors and other peptides. For example, precipitation using cold ethanol is the basis of the traditional Cohn fractionation method for preparation of albumin and other proteins from plasma.

Consequently, these methods have disadvantages, or are otherwise not well suited, for general enrichment of growth factors and other low molecular weight polypeptides.

Ultrafiltration and GFC both require expensive capital investment, are sensitive to fouling, and the latter results in dilution of the desired low molecular weight fraction. Other chromatographic fractionation systems can also be expensive to operate, and tend to be used to purify specific peptides rather than isolate high or low molecular weight fractions.

Liquid phase partitioning in multiphase systems (e.g. cloud point extraction and aqueous two-phase systems) is particularly of use when a labile protein (e.g. an enzyme) is the desired product as the protein is retained throughout in an aqueous environment, Scopes R.K. (1987), Tani H. et al. (1997). This assists with the retention of the biological activity of the molecule. The disadvantage of the method is that the desired product is obtained in the presence of large amounts of detergents, salts and/or water-soluble polymers which must be removed. This adds to the cost of the process and frequently necessitates the use of additional steps such as ultrafiltration.

The other remaining methods also all result in addition of large amounts of other chemicals (organic solvent, amino acids or salts) which must be removed from the solution of polypeptide. As well as increasing costs due to the need for additional processing steps, these may introduce safety issues as in the case of the use of large volumes of flammable and/or toxic solvents. The safe handling and eventual removal of such solvents requires the use of specially designed, and typically very expensive, processing facilities and equipment.

All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

SUMMARY OF THE INVENTION

The shortcomings of these various methods for removal of larger proteins from tissue extracts, when low molecular weight peptides are the peptides of interest, lead the inventors to consider a novel alternative. Namely, the prevention of the initial dissolution of higher molecular weight fraction proteins, by in situ denaturation within the tissue, by an organic solvent (preferably ethanol), prior to aqueous extraction. Treatment of solid tissue with organic solvent has been used previously, but specifically for the delipidation and dehydration of the tissue (Scopes, R.K. (1987), Betzing, H. et al (1975)) rather than enhancing the concentration of low molecular weight polypeptides in subsequent aqueous extracts. Consequently, further isolating of the LMW peptides is required.

According to one aspect of the present invention there is provided a process for isolating low molecular weight ("LMW") peptides from tissue in situ, comprising the steps of:
  a) homogenizing the tissue;
  b) mixing the homogenized tissue with an organic solvent to form a fully-wetted slurry;
  c) standing or agitating the slurry to denature the proteins in situ within the tissue;
  d) removing the organic solvent from the tissue;
  e) mixing the organic solvent-treated tissue of step d) with a sufficient volume of water or an aqueous solution to extract the peptides;
  f) separating a liquid extract from the tissue residue of step e) to obtain an aqueous solution containing the low molecular weight peptide fraction removed from the tissue.

Throughout this specification the terms "peptide", "polypeptide" and "protein" are used interchangeably and refer to a molecule which comprises at least one chain of one or more amino acids.

The term "isolated" means substantially separated, or purified away from, high molecular weight peptides or other unwanted material within the tissue from which the low molecular peptides are extracted.

Throughout this specification the term "low molecular weight peptide" or "LMW peptide" refers to a peptide having an apparent molecular weight of substantially 10,000 Daltons or below.

Throughout this specification the term "apparent molecular weight" as used herein refers to the molecular weight of a peptide as determined by gel filtration chromatography.

Throughout this specification the term "total protein extract" as used herein refers to a tissue extract prepared using standard prior art aqueous extraction techniques, such as detailed earlier in the background art discussion, without any attempt to control the molecular weights of the proteins contained in the extract.

Throughout this specification the term "agitating" or grammatical variations of this term refers to the process of stirring, shaking or irradiating with ultrasound in order to achieving a mixing effect.

It should be recognised by those skilled in the art that other water-soluble (non-peptide) components ("NPCs") may also be isolated along with the LMW peptides prepared using the process of the present invention. In some instances these NPCs may actually be desired components of the extraction process along with, or instead of, LMW peptides.

The tissue may be any animal tissue, or other substantially solid animal product (including, but not confined to, dried blood, milk or colostrum) from which it is desired to extract LMW peptides.

In general, the tissue may be homogenised via ultrasound or mechanical disruption so that it is finely divided. For example, the tissue may be homogenized via a mortar and pestle, blender, mill or any other suitable equipment. However, this list should not be seen as limiting.

In general, prior to homogenizing, the tissue may first be optionally subjected to a drying pre-step to assist with homogenization or with preservation of the tissue.

The tissue may be dried by any process which is capable of removing water therefrom, without affecting the properties of the LMW peptides of interest within the tissue.

In preferred embodiments the tissue may be freeze dried so as to not affect any heat sensitive growth factors.

The organic solvent may be any organic solvent which does not affect the properties of the LMW peptides of interest.

In some embodiments the organic solvent may be acetone, acetonitrile, methanol, propan-1-ol, propan-2-ol, however, this list should not be seen as limiting.

In preferred embodiments, the organic solvent may be ethanol due to its anti-microbial activity and low toxicity. Most preferably, in the case of dried tissue 70% ethanol may be used.

In embodiments, where the extraction process of the present invention is used in relation to fresh tissue, sufficient absolute ethanol may be added to provide a total water content of approximately 30% with respect to the volume of ethanol. Optionally, once this water content has been achieved, further 70% ethanol can be added, if required, to create a fully-wetted loose slurry.

It will be appreciated by those skilled in the art that whilst higher or lower concentrations of ethanol may optionally be used: the maximal anti-microbial activity of ethanol occurs at the preferred concentration of 70% ethanol.

For ease of reference only the organic solvent will now simply be referred to as being ethanol.

Throughout this specification the term "fully-wetted" refers to the addition of sufficient liquid to a finely divided solid so as to produce a free flowing slurry.

The term "liquid phase" as used herein refers to the use of solutions of materials that are normally solids (for example, proteins), so that processing operations are performed entirely with liquids.

Throughout this specification the term "ambient temperature" shall mean the temperature of the encompassing environment and shall substantially be in the range 10-30° C.

In general, the fully-wetted slurry may be left to stand or is agitated for a period of at least substantially one hour at an ambient temperature. Most preferably the fully-wetted slurry is left to stand or is agitated at least substantially three or more hours, and at an ambient temperature. However, the performance of this step at a lower temperature (i.e. below that of the ambient environment), if necessary to maintain biological activity of the LMW peptides, is not precluded by this method. In preferred embodiments agitation is the preferred over simply allowing the slurry to stand, as it would be reasonably expected by those skilled in the art to lead to more efficient extraction of soluble components from tissue.

It will be appreciated by those skilled in the art that the period over which the fully-wetted slurry is left to stand, should be sufficient to allow for the denaturing of the proteins to incur in situ within the tissue. As well as to reduce the microbiological loading of the slurry. After the fully-wetted slurry has been left to stand, the ethanol may be removed in a variety of different manners.

In some embodiments the ethanol may be removed by filtration, centrifugation, or other physical means. However, it should be appreciated that removing ethanol in this manner may result in a lower yield of LMW peptides in the final aqueous solution. As some dissolution of hydrophobic or LMW peptides into the organic solvent may occur.

Thus, in preferred embodiments the ethanol may be removed via direct evaporation of the organic solvent under vacuum. Most preferably, the evaporation may be achieved using only a gentle heat, so that the temperature remains below substantially 30° C., where preservation of heat sensitive growth factors is an objective.

Once the ethanol has been removed, the ethanol treated tissue may be fully dried under a high vacuum, for example in a freeze drier or such like. This optional step is recommended where it is desired to remove traces of the organic solvent to facilitate the storage of the tissue at this stage, or to reduce the chances of the traces of organic solvent affecting yield or composition of the LMW peptides obtained in the final water based extraction of the remaining method steps f) or method step g) this later step being detailed below.

The term "aqueous solution" as used herein refers to a solution in which the solvent used is water and includes aqueous salt or buffer solutions.

In some preferred embodiments there may be an additional step d1) wherein the solvent treated tissue of step d) may be fully dried prior to undertaking step e).

The ethanol treated tissue of steps d) or d1) may be mixed with water or with suitable aqueous salt or buffer solution (including but not limited to: phosphate buffer, citrate buffer, acetate buffer, tris buffer or dilute sodium chloride solution). The resulting mixture should preferably be stirred for substantially one hour. For preservation of growth factors, this should again be performed done at low temperature—i.e. ambient temperature or below.

It is envisaged that a liquid extract may be separated from the ethanol treated tissue of step e) in a variety of different ways.

For example, the liquid extract may be separated (i.e. isolated from the solid residue) by:
  decantation;
  centrifugation;
  filtration; or
  other suitable processes as would be apparent to a person skilled in the art.

Most preferably, the liquid extract may be clarified by centrifugation, fine filtration or any other suitable clarification process.

In some preferred embodiments there may be an additional step g) wherein steps e) to f) may be repeated, one or more times, to improve the yield of liquid extract from the tissue residue of step e).

Once the solutions of low molecular weight peptides have been obtained from steps f) or g) the liquid extract may optionally be dried for storage or further processing (e.g. product formulation) purposes.

In preferred embodiments the liquid extract from steps f) or g) maybe dried in order to obtain low molecular weight peptides.

Most preferably the drying of the solutions of low molecular weight peptides from steps f) or g) may be achieved via freeze drying, although other drying means are possible depending on the properties of the low molecular weight peptides of interest.

In a further aspect the present invention also provides an isolated mixture of low molecular peptides obtained by the process.

In yet another aspect the present invention provides the use of an organic solvent to denature proteins in situ within tissue as part of an extraction process to isolate low molecular weight peptides from tissue.

Thus, preferred embodiments of the LMW in situ extraction process of the present invention may have a number of advantages over the prior art extraction processes which can include:

1. Providing a simple method for obtaining an isolated LMW peptide extract with a higher concentration of LMW peptides, than is achieved using the current methods of extraction.
2. Providing a method which specifically targets the isolation of LMW peptides.
3. Providing a method which minimises the use of large amounts of expensive or dangerous reagents.

BRIEF DESCRIPTION OF DRAWINGS

Further aspects of the present invention will become apparent from the following description which is given by way of example only and with reference to the accompanying drawings in which.

DETAILED DESCRIPTION OF THE PREFERRED EMBODIMENT

Figure 1:
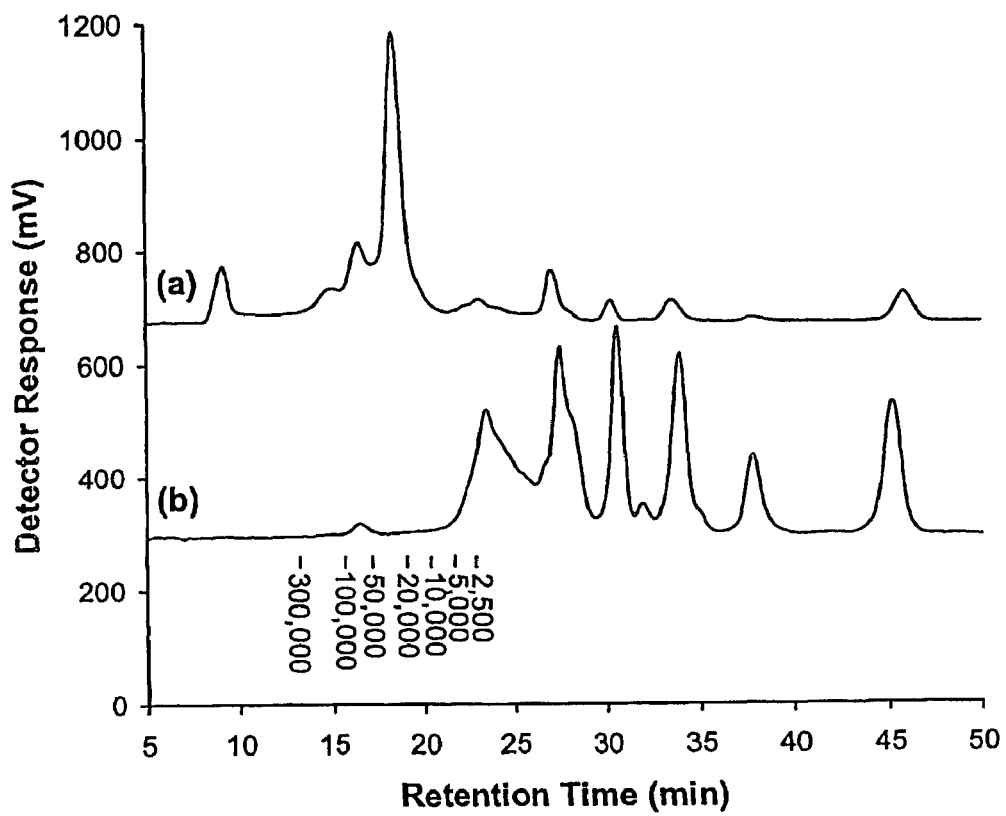
FIG. 1(a) Shows a gel filtration chromatography profile of deer velvet total protein extract.
FIG. 1(b) Shows a deer velvet LMW extract prepared using the new in situ extraction process of the present invention and an approximate molecular weight scale is given below each chromatogram.

Best Modes for Carrying Out the Invention

Experimental

LMW in situ Extraction Process—Heat Dried and Freeze-Dried Deer Velvet

Ground deer velvet powder (5.00 g) derived from the mid-portion of a traditionally (heat) dried antler was weighed into a 500 Ml Buchi evaporating flask. Sufficient 70% ethanol (~30 Ml) was added to create a mobile slurry and the mixture was stirred at ambient temperature (20° C.) on a magnetic stirrer for one hour. The solvent was then removed by rotary evaporation using a Buchi Rotavapor with a 30° C. water bath. Traces of residual solvent were removed under high vacuum by use of an oil pump (Edwards) for one hour. De-ionised water (100 Ml) was added to the dried residue and the mixture was stirred at ambient temperature (20° C.) on a magnetic stirrer for three hours. Following filtration through glass fibre filter paper (Whatman GF/A) the filtrate was centrifuged at 14,600 g for 30 Minutes at 4° C. The supernatant was decanted into a glass bottle and then shell frozen and freeze-dried in a cabinet freeze drier (Cuddon) to provide the LMW Extract of Deer Velvet (0.297 g, 5.9% yield) as a brown slightly "sticky" solid. The IGF-1 content of the LMW extract obtained was measured at 0.32 µg/g—refer Table 1.

The above extraction process was repeated with a composite ground deer velvet powder (5.00 g) derived from freeze-dried antlers. The LMW Extract (0.312 g, 6.2%) was obtained as a free-flowing brown solid. The IGF-1 content of the LMW extract obtained was measured at 3.4 µg/g—refer Table 1.

TABLE 1

IGF-1 and TGFβ$_2$ concentrations in the raw material (i.e. velvet powder) and in LMW extract obtained from the raw material by the process of the present invention.

| Growth Factor | Velvet | Velvet Powder | LMW Extract |
| --- | --- | --- | --- |
| IGF-1 | Heat Processed | 0.18 µg/g | 0.32 µg/g |
|  | Freeze Dried | 1.1 µg/g | 3.4 µg/g |
| TGFβ$_2$ | Heat Processed | 7.9 ng/g | 47.6 ng/g |

Small Scale LMW in situ Extraction Process Used in Comparisons of Extraction Conditions An accurately weighed amount (500 Mg) of tissue (deer velvet, deer placenta, sheep liver) or freeze-dried deer blood was added to a glass tube fitted with a teflon-lined cap. Sufficient organic solvent was added to provide the required ratio (v/w) with respect to the solid material, and the mixture was agitated on a Vibramax mixer (IKA) for the required period of time at ambient temperature (20° C.). In most instances, and unless otherwise stated, 3 Ml of solvent was added (6:1 ratio, v/w), and mixing was performed for 3 hours. The bulk of the organic solvent was then removed using a vacuum centrifuge (Heto) and remaining traces of organic solvent were removed under high vacuum using a freeze-drier (FTS).

To the organic solvent-treated test material was added 10 Ml of aqueous buffer. In most instances, and unless otherwise stated, the buffer used was 0.05M phosphate buffer (pH 6.9).

The mixture was agitated on a Vibramax mixer (IKA) for 1 hour at ambient temperature (20° C.), and was then centrifuged at 2,000 g for 15 Minutes at 4° C. The supernatant was transferred to a clean tube and was centrifuged at 40,000 g for 15 Minutes at 4° C. The fully clarified supernatant was then aliquoted into clean tubes prior to analysis by GFC (as detailed below) or for growth factors. In some experiments, a 5.0 Ml aliquot was also fully dried in pre-weighed tubes using a vacuum oven for determination of extract yields.

In most experiments, the test material was also extracted with aqueous buffer, as detailed above, without prior treatment with organic solvent. These samples served as control samples to determine the efficiency of removal of high molecular weight proteins by the solvent pre-treatment.

Analysis of Low Molecular Weight Extracts

The low molecular weight extracts were analysed by GFC on a Superose 12 HR 10/30 column (Amersham Biosciences) using either 0.05M phosphate buffer (pH 6.9) containing 0.3M sodium chloride and 0.05% sodium azide, or 0.05M ammonium bicarbonate for elution. Solid extract samples were dissolved in phosphate buffer at a concentration of approximately 5 Mg/ml and 10 μl of each solution were injected onto the column and eluted at a flow rate of 0.75 Ml/min. Extract solutions prepared using the small scale LMW in situ extraction process were directly injected (10 μl) and eluted under similar conditions. Proteins were detected by measurement of UV absorption at 280 nm.

Molecular weight calibration of the Superose 12 column was performed by separation of a standard mixture of known proteins of known molecular weights under the above conditions. A calibration curve was then constructed by plotting the logarithm of protein molecular weight against retention time. Apparent molecular weights of eluted protein peaks were determined by interpolation using the calibration curve.

An automated data processing method was developed using Turbochrom 4.1 (PE Nelson) for comparison of the proportions of low molecular weight proteins and of high molecular weight in the extracts. The method summed the areas of all of the peaks having retention times less than 20.5 Minutes ("high molecular weight" peaks, due to proteins having molecular weights greater than approximately 8,000 Daltons) and those with retention times greater than 20.5 Minutes ("low molecular weight" peaks, due to proteins having molecular weights less than approximately 8,000 Daltons) in chromatograms of samples eluted using phosphate buffer. For samples eluted with ammonium bicarbonate, the equivalent split between high molecular weight and low molecular weight peaks was performed at a retention time of 18.5 Minutes.

Prior Art—Preparation of Deer Velvet Total Protein Extract for GFC Analysis

Freeze-dried deer velvet powder (0.1 g) was briefly mixed with 0.05M phosphate buffer (pH 6.9, 3 Ml) by use of a vortex mixer. Following centrifugation at 2,000 g for 5 minutes the mixture was sonicated in an ultrasound cleaning bath (Crest Ultrasonics) for 1 hour at 20° C. The total protein extract thus prepared was clarified by centrifugation at 12,700 g for 15 Minutes at 4° C. The supernatant was then directly analysed by GFC—refer FIG. 1a). The total protein extract procedure was based on the prior art methods for extraction of proteins as outlined in Scopes, R.K. (1987).

Prior Art—Precipitation of High Molecular Weight Proteins by Ethanol from Deer Velvet Total Protein Extract in the Liquid Phase for GFC Analysis.

A total protein extract of deer velvet was prepared by gently shaking dried deer velvet powder (10 g) in de-ionised water (100 Ml) for 3 hours at ambient temperature. The mixture was centrifuged at 2,100 g for 15 Minutes and the supernatant was decanted into a second centrifuge bottle. This was centrifuged at 21,000 g for 15 Minutes in order to clarify the water extract, which was then chilled to 4° C. Cold 100% ethanol (3 volumes) was gradually added with constant stirring. The cloudy mixture was centrifuged at 21,000 g for 30 Minutes at 4° C. to remove the precipitated protein. The supernatant was then evaporated to dryness on a Buchi rotary evaporator prior to analysis by GFC—refer FIG. 2. The total protein extract procedure was based on the prior art methods for extraction of proteins as outlined in Scopes, R.K. (1987).

IGF-1 Analysis

Samples were analysed for insulin-like growth factor 1 (IGF-1) by Endolab (Canterbury Health Laboratories) using a radioimmunoassay for human IGF-1. The assay had an $ED_{50}$ of 0.39 μg/g and a detection limit of 0.02 μg/g for freeze dried extract samples. For extract solutions, the $ED_{50}$ of the assay was 50 μg/L and the detection limit was 4.1 μg/L.

IGF-2 Analysis

Samples of extract solutions were analysed for insulin-like growth factor 2 (IGF-2) by Endolab (Canterbury Health Laboratories) using a radioimmunoassay for human IGF-2. The assay had an $ED_{50}$ of 1132 μg/L and a detection limit of 32 μg/L.

EGF-like Activity Analysis

Samples of extract solutions were analysed for epidermal growth factor-like (EGF-like) activity using a radio-receptor assay. The assay measures the ability of substances in the sample to displace radioactively labelled mouse EGF (Amersham) from its receptor on A431 cells (epidermoid carcinoma cell line) in culture. Because other growth factors may bind to the EGF receptor, the combined activity is measured as EGF-like activity.

$TGF\beta_1$ Analysis

Samples were analysed for transforming growth factor $\beta_1$, ($TGF\beta_1$) using the $E_{max}$® Immunoassay System (Promega Corporation). The assay was specific for $TGF\beta_1$ ($\leq 1.6\%$ cross reactivity with $TGF\beta_2$ and $\leq 0.7\%$ $TGF\beta_3$) and had a detection limit of 32 pg/ml.

$TGF\beta_2$ Analysis

Samples were analysed for transforming growth factor $\beta_2$ ($TGF\beta_2$) using the $E_{max}$® Immunoassay System (Promega Corporation). The assay was specific for $TGF\beta_2$ ($\leq 3\%$ cross reactivity with $TGF\beta_1$ and $TGF\beta_3$) and had a detection limit of 32 pg/ml 20 (equivalent to 0.32 ng/g in solid samples).

RESULTS

IGF-1 and $TGF\beta_2$

A comparison between the IGF-1 and $TGF\beta_2$ contents of low molecular weight (i.e. new process) extracts prepared from freeze dried and/or heat processed deer velvet powder using the new extraction process are given in Table 1 above. In each case the LMW extracts prepared by the new method had higher concentrations of immunoreactive IGF-1 and $TGF\beta_2$ than was measured in the deer velvet powders from which they were prepared.

Molecular Weight Distribution in Deer Velvet Low Molecular Weight Extract Prepared Using the New Process of the Present Invention The gel filtration profile of a water extract of deer velvet powder pre-treated with 70% ethanol (i.e. prepared using the new process) is compared with a comparable extract of untreated velvet powder in FIG. 1. As can be seen from FIG. 1(a), proteins with apparent molecular weights greater than 10,000 Daltons comprise the bulk of water-based total protein extract obtained from deer velvet at non-elevated temperatures. In comparison, essentially all of these higher molecular weight proteins are absent in the low molecular weight extract prepared using the new ethanol pre-treatment process (FIG. 1(b)).

Figure 2:
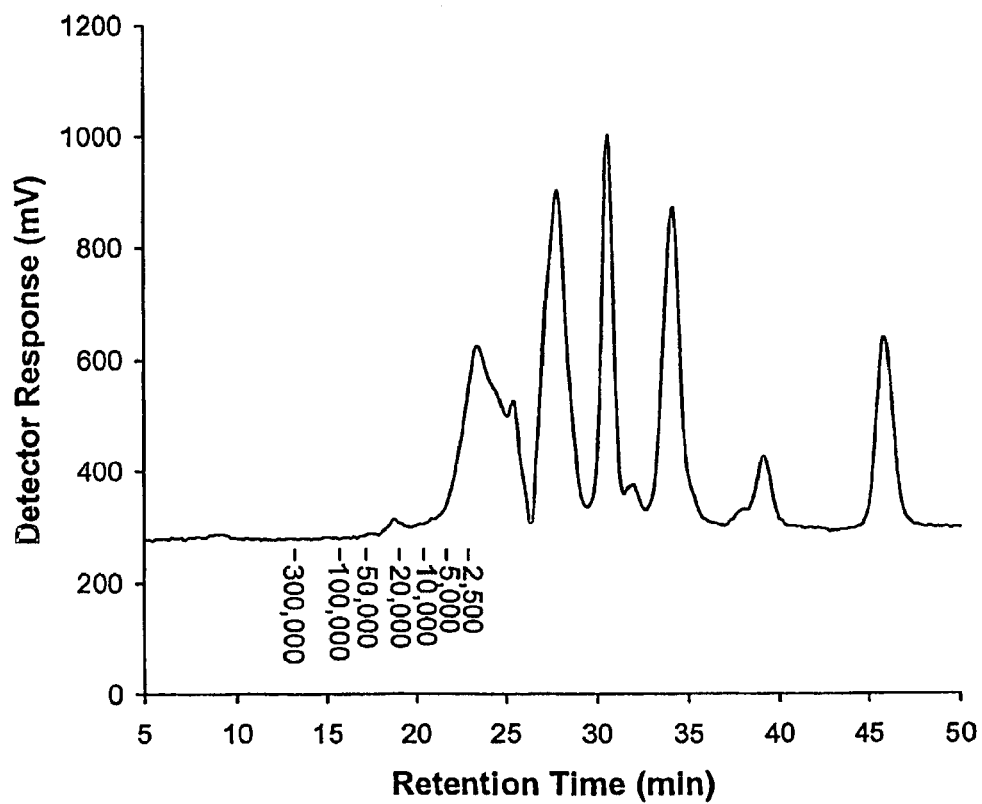
FIG. 2 A LMW extract prepared by precipitation of high molecular weight proteins from deer velvet total protein extract by addition of cold ethanol in the liquid phase.

Precipitation of high molecular weight proteins from standard aqueous deer velvet extract in order to isolate LMW peptides was performed in the liquid phase. This process was undertaken in order to compare the weight distribution of proteins removed by this standard prior art protein chemistry technique with that of the new process of the present invention. As shown in FIG. 2, addition of a 3:1 ratio of ethanol to an aqueous solution of velvet total protein extract also resulted in essentially complete removal of proteins having molecular weights over 10,000 Daltons. The close similarity between the two GFC chromatograms in FIGS. 1(b) and 2 demonstrates that, in the new extraction process of the present invention, ethanol renders the same spectrum of higher molecular weight proteins insoluble (in situ within the tissue) as it does in the liquid phase.

Figure 3:
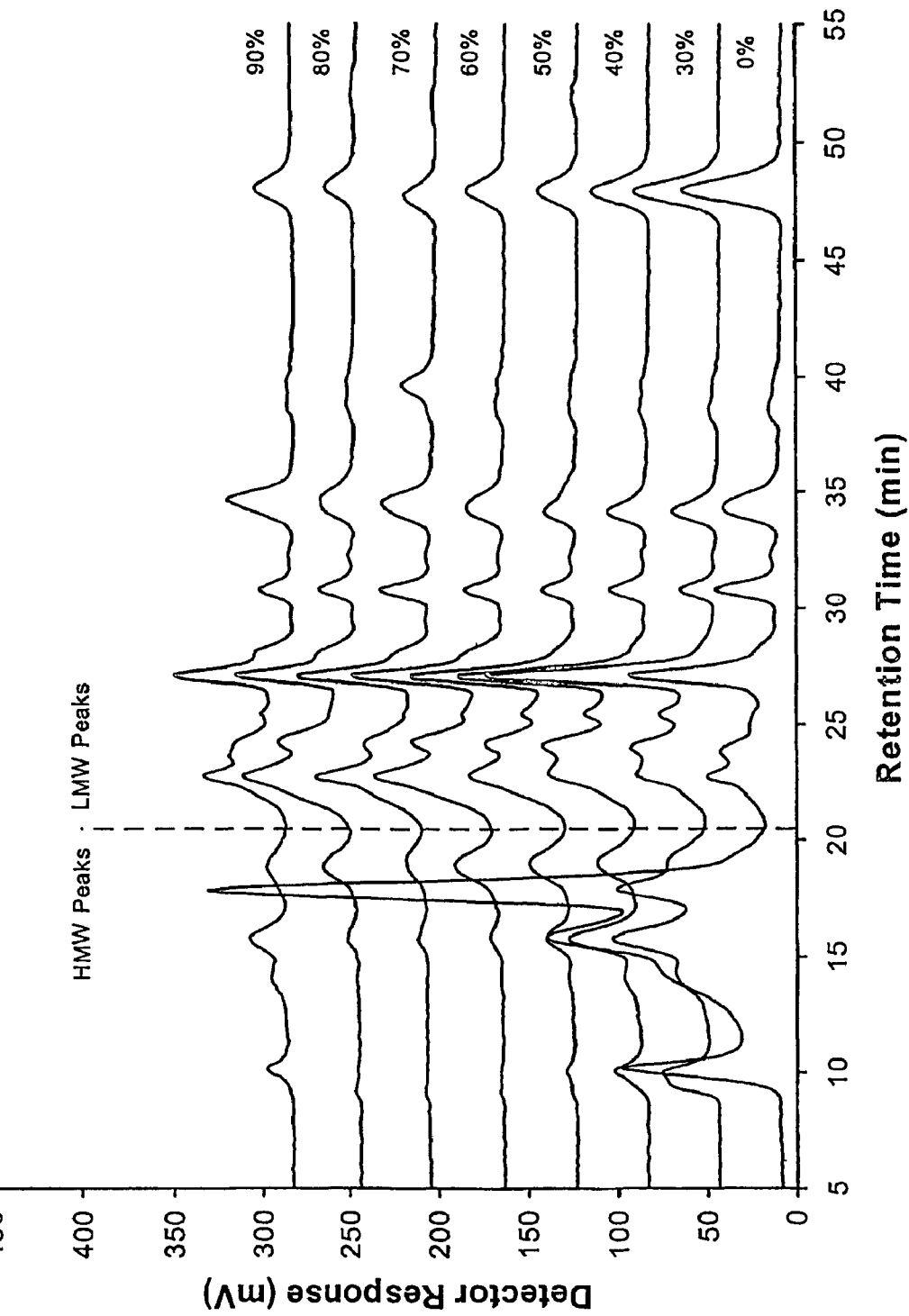
FIG. 3. Shows gel filtration chromatography profiles of deer velvet LMW extracts prepared using the new in situ extraction process, and with varying concentrations of ethanol in the pre-treatment incubation step (which was performed for 3 hours) (Gel filtration chromatography profiles of freeze-dried deer velvet samples extracted with 0.05M phosphate buffer (pH 6.9) following pretreatment for 3 hours with a 6:1 (v/w) ratio of 30%, 40%, 50%, 60%, 70%, 80% or 90% ethanol, or without pre-treatment (0% ethanol))

The Effect of the Concentration of Ethanol Used in the New Process of the Present Invention The gel filtration chromatography profiles of freeze-dried deer velvet samples extracted with 0.05M phosphate buffer (pH 6.9) following pre-treatment for 3 hours with a 6:1 (v/w) ratio of 30%, 40%, 50%, 60%, 70%, 80% or 90% ethanol, or without pre-treatment, are shown in FIG. 3. This figure demonstrates that at low concentrations (30%, 40%) and at high concentration (90%) of ethanol, the removal of high molecular weight proteins is less efficient than at intermediate concentrations (50-80%).

Figure 4:
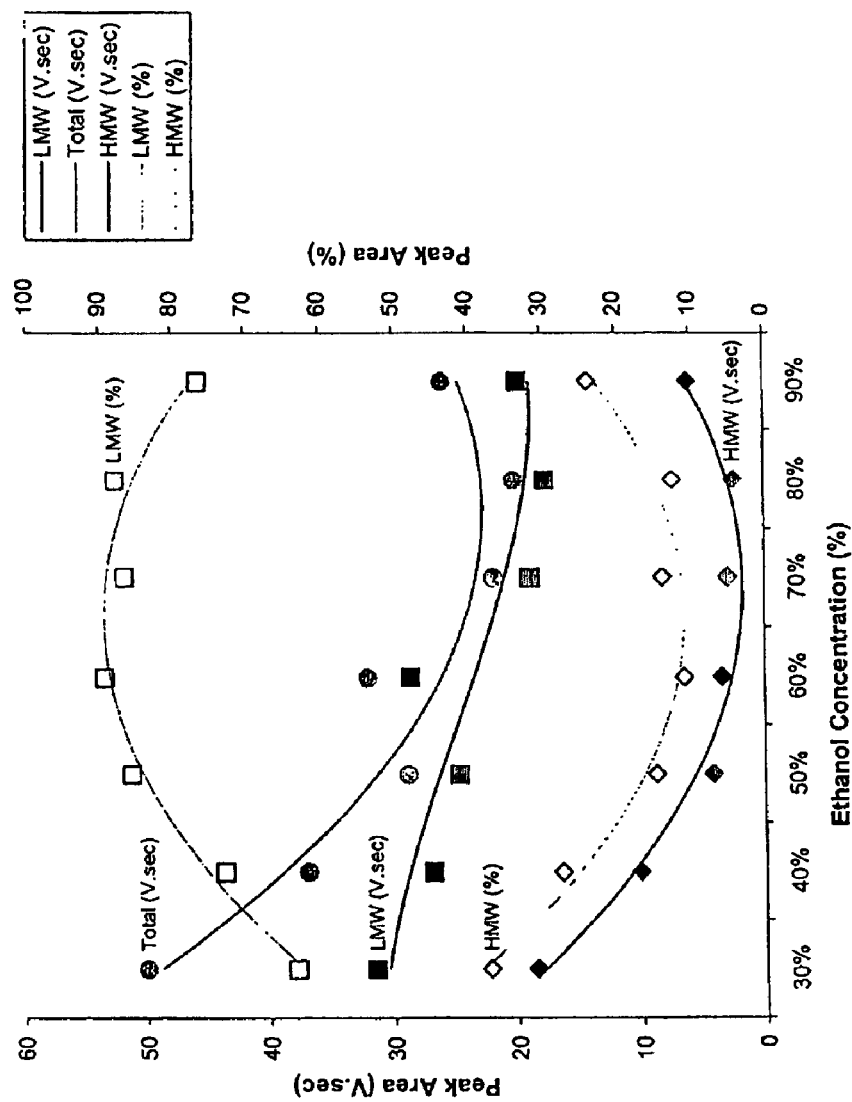
FIG. 4. Shows a graph showing the proportions of LMW and HMW proteins in deer velvet LMW extracts prepared using the new in situ extraction process, and with varying concentrations of ethanol in the pre-treatment incubation step (which was performed for 3 hours) (a graph showing the effect of pre-treatment of freeze-dried deer velvet samples with 30%, 40%, 50%, 60%, 70%, 80%, or 90% ethanol (6:1 v/w), prior to extraction with 0.05M phosphate buffer (pH 6.9), on the total areas of peaks of low and of high molecular weight proteins in the extract solutions)

As shown in FIG. 4, the percentage of the total combined peak area that is due to low molecular weight proteins reaches a maximum at around 60-70% ethanol. The absolute area (expressed in V.sec) of the low molecular weight peaks, which is proportional to the combined concentrations of the substituent proteins, declines slightly as the concentration of ethanol is increased from 30% to 90%. In contrast, the absolute area (expressed in V.sec) of the high molecular weight peaks declines sharply as the concentration of ethanol is increased from 30 to 50%, is stable at a low level in the range 50-80% ethanol, and then increases again slightly in the sample prepared using 90% ethanol.

Figure 5:
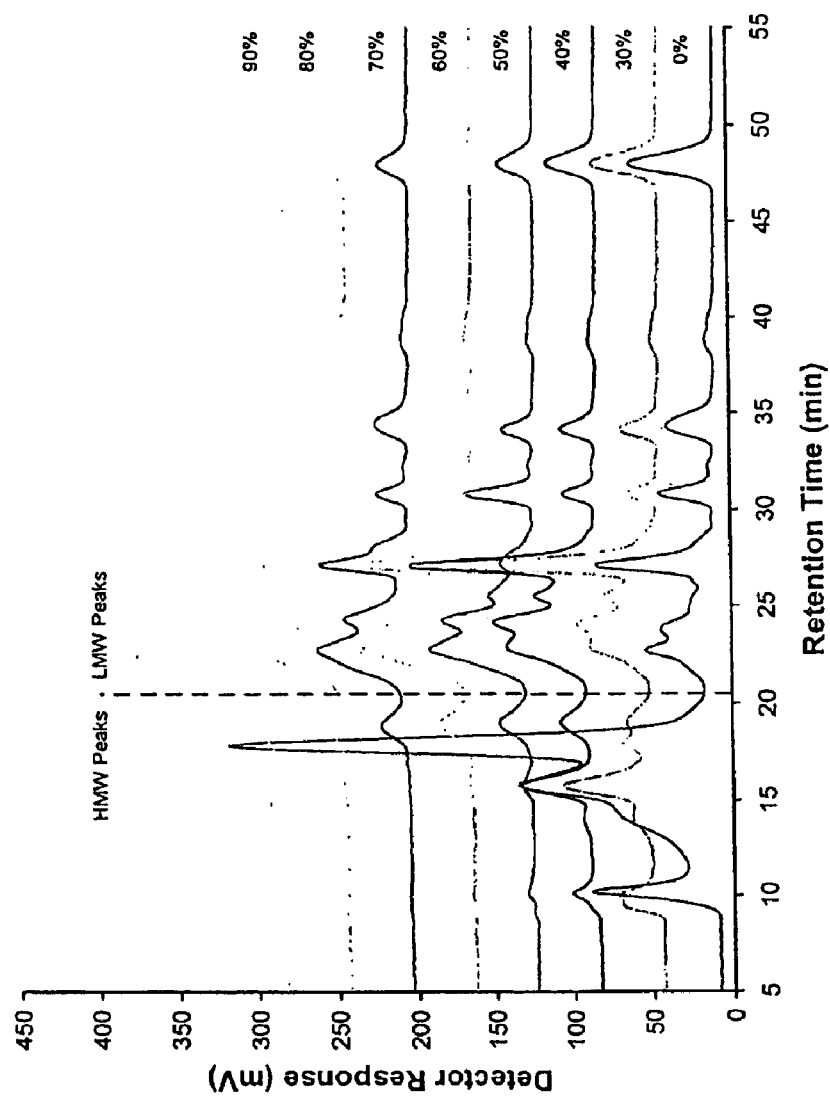
FIG. 5. Shows gel filtration chromatography profiles of deer velvet LMW extracts prepared using the new in situ extraction process, and with varying concentrations of ethanol in the pre-treatment incubation step (which was performed for 16.5 hours), (gel filtration chromatography profiles of freeze dried deer velvet samples extracted with 0.05M phosphate buffer (pH 6.9) following pre-treatment for 16.5 hours with a 6:1 (v/w) ratio of 30%, 40%, 50%, 60%, 70%, 80%, or 90% ethanol, or without pre-treatment (0% ethanol))

The Effect of the Incubation Time With Ethanol in the New Process of the Present Invention The above experiment was repeated using overnight (16.5 hours) pre-treatment of the velvet with the various concentrations of ethanol prior to buffer extraction, instead of 3 hours pre-treatment. As can be seen by comparing FIG. 5 with FIG. 3, the increased pre-treatment period resulted in only a very slight change in the gel filtration chromatography profiles of the extract solutions. The most evident change is the more efficient removal of high molecular weight proteins that elute from the chromatography column prior to 17 Minutes, relative to samples prepared using the 3 hour pre-treatment period.

Figure 6:
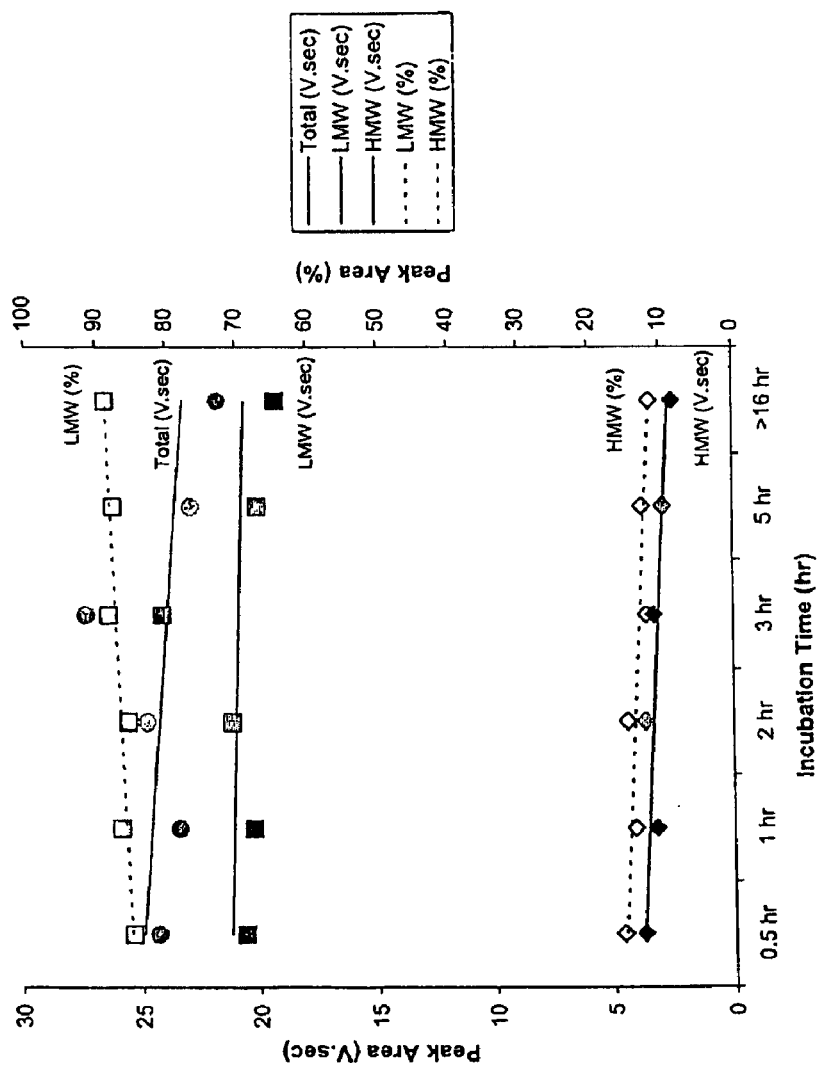
FIG. 6. Shows a graph showing the proportions of LMW and RMW proteins in deer velvet LMW extracts prepared using the new in situ extraction process, and with varying periods of incubation with 70% ethanol in the pre-treatment incubation step (a graph showing the effect of incubation used for the pretreatment of freeze-dried deer velvet samples with 70% ethanol, prior to extraction with 0.05% phosphate buffer (pH 6.9), on the total areas of peaks of low and of high molecular weight proteins in the extract solutions)

The result of varying the incubation time with 70% ethanol on the proportions of low molecular weight and high molecular weight proteins is shown in FIG. 6. The absolute peak area (in V.sec) of the low molecular weight proteins remained essentially constant for incubation periods between 30 Minutes and over 16 hours (overnight), but as a proportion these peaks slightly increased with time. This was due to a gradual concomitant decline in the absolute peak area (in V.sec) of the high molecular weight proteins, due to more efficient removal of these protein with increased ethanol incubation times.

Figure 7:
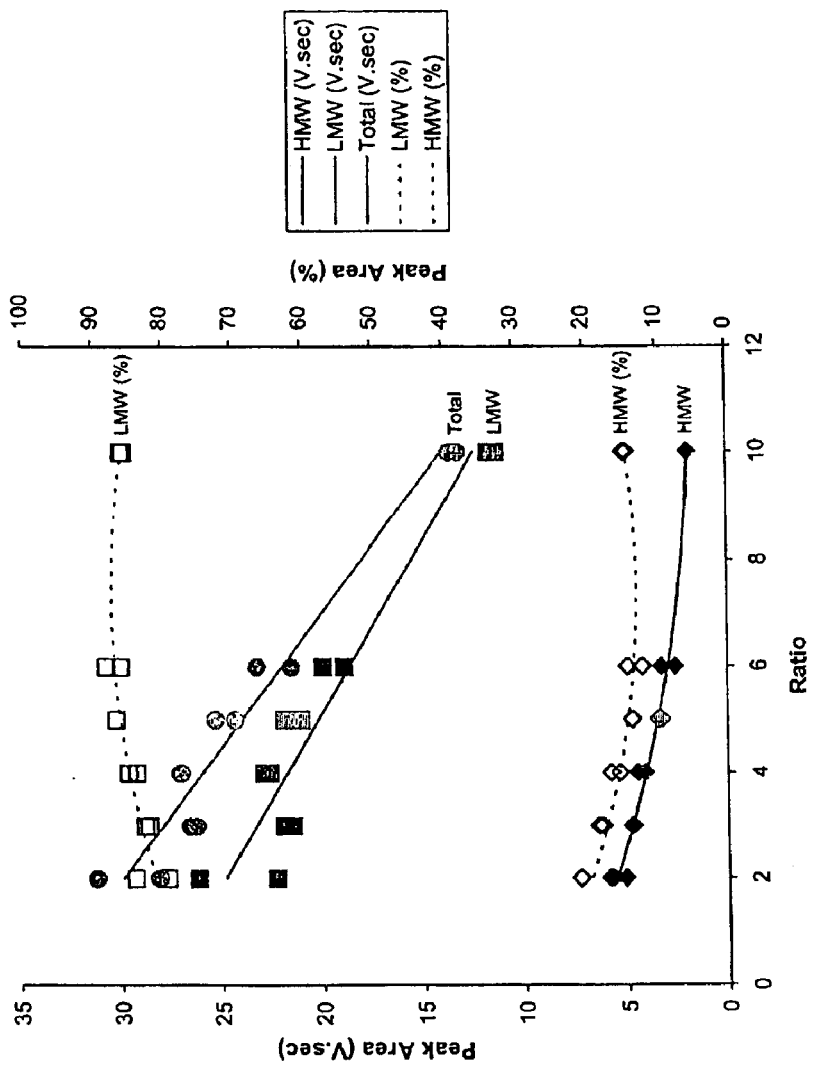
FIG. 7. Shows a graph showing the proportions of LMW and HMW proteins in deer velvet LMW extracts prepared using the new in situ extraction process, and with varying ratios of 70% ethanol to deer velvet tissue in the pre-treatment incubation step (a graph showing the effect of the ratio (v/w) of the 70% ethanol used for 3 hour pre-treatment of freeze-dried deer velvet samples, prior to extraction with 0.05M phosphate buffer (pH 6.9), on the total areas of peaks of low and of high molecular weight proteins in the extract solutions)

The Effect of the Ratio of Ethanol Used in the New Process of the Present Invention FIG. 7 shows the effect of varying the ratio of 70% ethanol used in the new process, between 2:1 and 10:1 (v/w) with respect to the amount of freeze-dried deer velvet tissue extracted. The proportions of low molecular weight and high molecular weight peaks in the final extract remain moderately constant across the whole range, but the absolute peak areas steadily decline. The effect is greatest on the area of the peaks due to low molecular weight proteins, which indicates a reduction in yield of these proteins with increasing ratio of ethanol to tissue.

Figure 8:
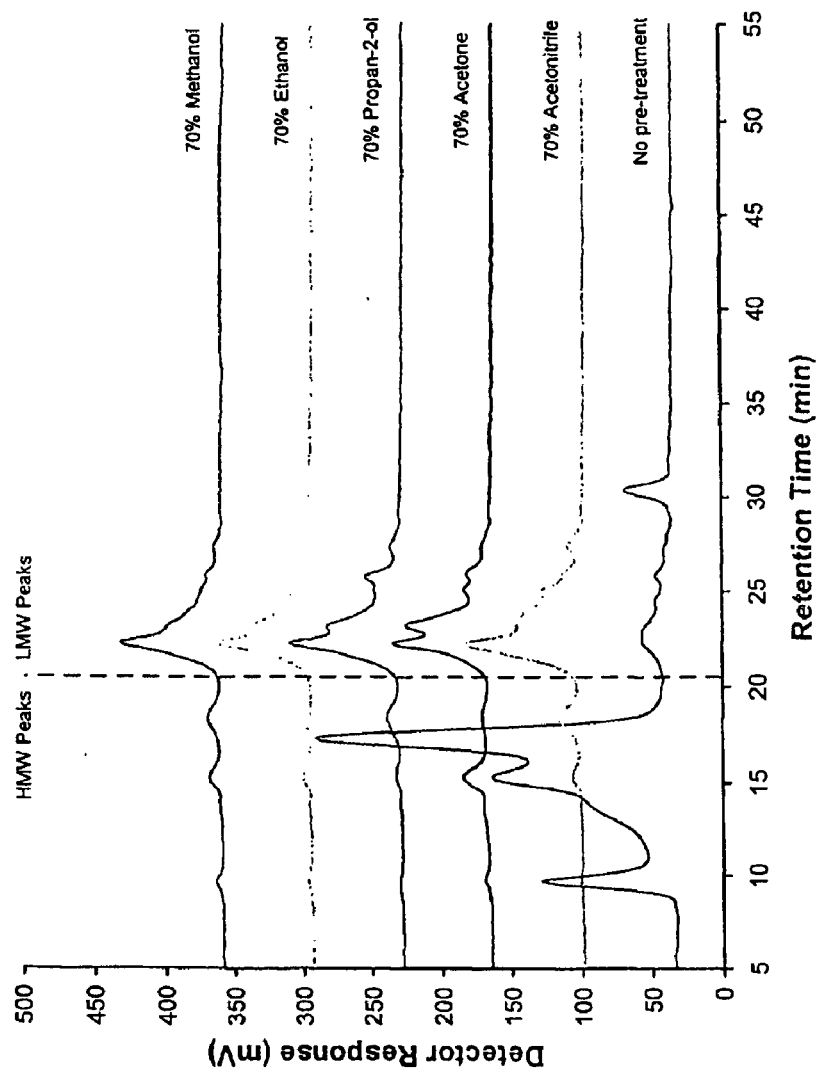
FIG. 8. Shows gel filtration chromatography profiles of deer velvet LMW extracts prepared using the new in situ extraction process, and with varying organic solvents in the pre-treatment incubation step (gel filtration chromatography profiles of freeze-dried deer velvet samples extracted with 0.05M) phosphate buffer (pH 6.9) following pre-treatment for 3 hours with a 6:1 (v/w) ratio of 70% acetonitrile, 70% acetone, 70% propan-2-01, 70% ethanol or 70% methanol, or without pre-treatment with organic solvent)

The Effect of the Organic Solvent Used in the New Process of the Present Invention FIG. 8 compares the effect of using 70% acetonitrile, 70% acetone, 70% propan-2-ol or 70% methanol instead of 70% ethanol for pre-treatment of freeze-dried deer velvet on the protein profiles of the resultant phosphate buffer extracts. A very similar range of high molecular proteins is missing in each of the extracts, showing that each solvent is effective in the new process.

Figure 9:
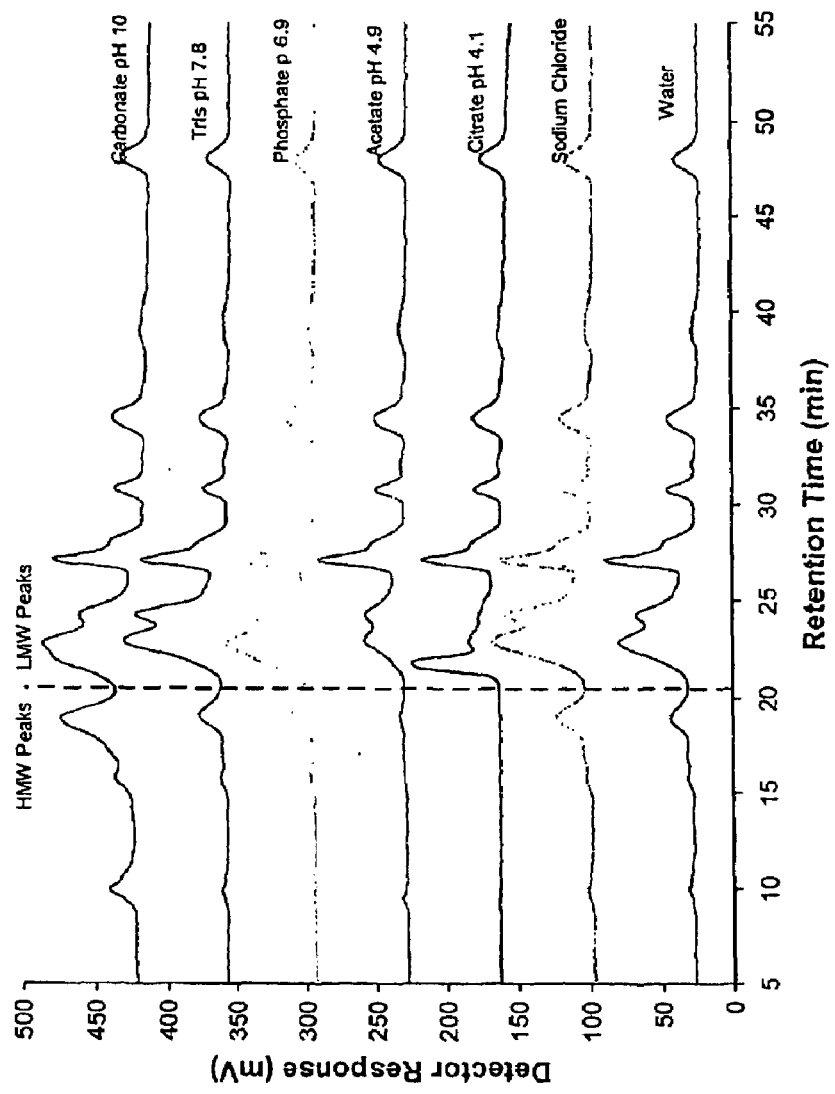
FIG. 9. Shows gel filtration chromatography profiles of deer velvet LMW extracts prepared using the new in situ extraction process, and with varying buffers used for the aqueous extraction step (gel filtration chromography profiles of freeze-dried deer velvet samples extracted with various buffers (each 0.05M) or with 0.05M sodium chloride or water, following pre- treatment for 3 hours with a 6:1 (v/w) ratio of 70% ethanol)

The Effect of the Aqueous Buffer Used in the New Process of the Present Invention FIG. 9 compares the effect of using water, 0.05M sodium chloride, 0.05M citrate buffer (pH 4.1), 0.05M acetate buffer (pH 4.9), 0.05M tris buffer (pH 7.8) or 0.05M carbonate buffer (pH 10.0) instead of 0.05M phosphate buffer (pH 6.9) for the aqueous extraction on the protein profiles of the resultant extracts. A very similar range of proteins is present in the extracts prepared at pHs near neutrality (using water, sodium chloride, or tris or phosphate buffers). However, fewer high molecular weight proteins are present in extracts prepared at lower pH (using citrate or acetate buffers), while in the extract prepared at higher pH (using carbonate buffer) a greater range of high molecular weight proteins is evident in the protein profile.

The yields and growth factor contents of each of the above extracts are given below in Table 2. In each case the yield has been calculated as the dry weight of the extract after correction for the content of added salts, and is expressed as a percentage of the starting weight of freeze-dried deer velvet powder. All extracts contained measurable levels of growth factors, although these varied according to the pH of the aqueous extraction medium. EGF-like activity was particularly high in extracts prepared at low pH (using citrate or acetate buffers) or high pH (using carbonate buffer).

TABLE 2

Yields, IGF-1, IGF-1, TGFβ$_1$, TGFβ$_2$ and EGF-like concentrations in extracts of deer velvet powder derived via the LMW extraction process of the present invention.

| Buffer | Yield | IGF-1 (ng/ml) | IGF-2 (ng/ml) | TGFβ$_1$ (ng/ml) | TGFβ$_2$ (ng/ml) | EGF-like (µg/ml) |
|---|---|---|---|---|---|---|
| Water | 5.0% | 11.5 | 64 | 0.31 | 0.53 | 75 |
| Sodium Chloride | 7.7% | 14.7 | 88 | 0.15 | 0.35 | 51 |
| Citrate (pH 4.1) | 13.5% | 9.5 | 77 | 0.60 | 0.57 | 750 |

TABLE 2-continued

Yields, IGF-1, IGF-1, TGFβ₁, TGFβ₂ and EGF-like concentrations in extracts of deer velvet powder derived via the LMW extraction process of the present invention.

| Buffer | Yield | IGF-1 (ng/ml) | IGF-2 (ng/ml) | TGFβ₁ (ng/ml) | TGFβ₂ (ng/ml) | EGF-like (µg/ml) |
|---|---|---|---|---|---|---|
| Acetate (pH 4.9) | 9.4% | 7.5 | 88 | 0.12 | 0.06 | 623 |
| Phosphate (pH 6.9) | 6.3% | 13.7 | 67 | 0.44 | 0.22 | 90 |
| Tris (pH 7.8) | 8.6% | 16.0 | 61 | 0.21 | 0.44 | 0 |
| Carbonate (pH 10) | 7.3% | 25.1 | 58 | 0.46 | 0.54 | 643 |

Use of the New Process With Materials Other Than Deer Velvet

Figure 10:
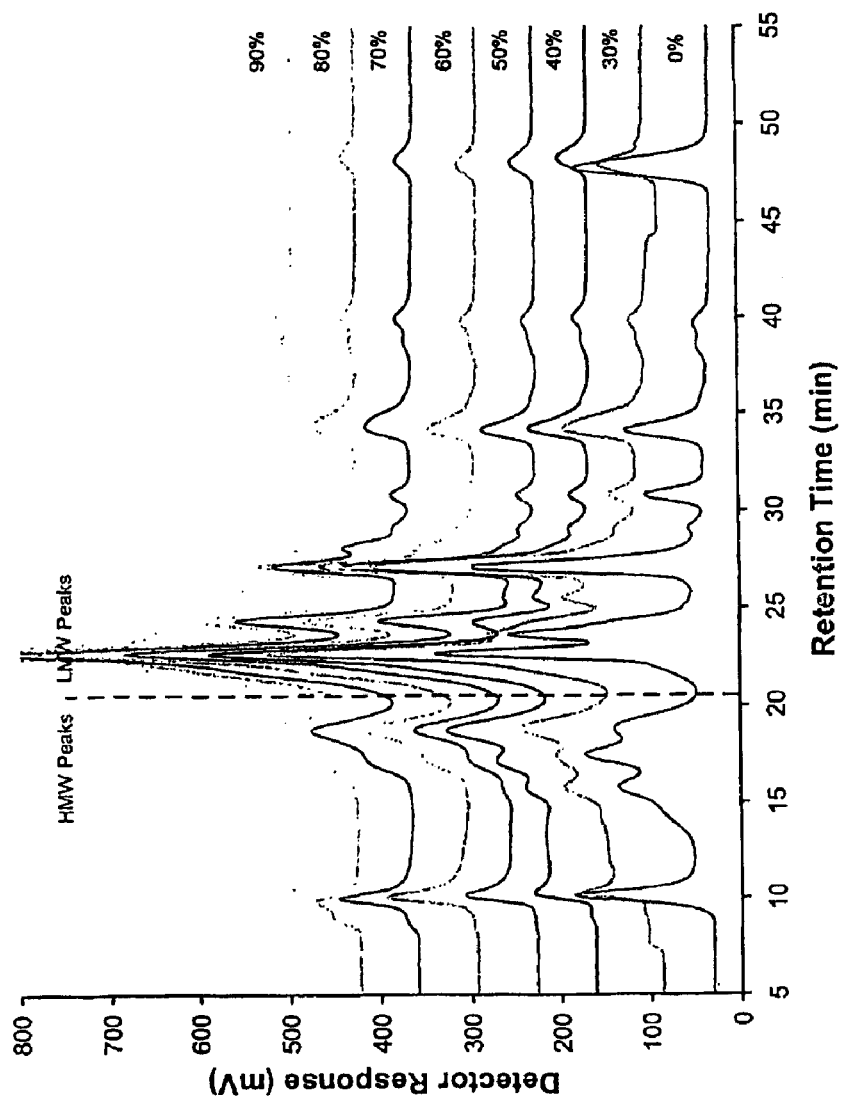
FIG. 10. Shows gel filtration chromatography profiles of deer placenta LMW extracts prepared using the new in situ extraction process, and with varying concentrations of ethanol in the pre-treatment incubation step (gel filtration chromatography profiles of freeze-dried deer placenta samples extracted with 0.05M phosphate buffer (pH 6.9) following pre-treatment for 3 hours with a 6:1 (v/w) ratio of 30%, 40%, 50%, 60%, 70%, 80%, or 90% ethanol, or without pre-treatment (0% ethanol))
Figure 11:
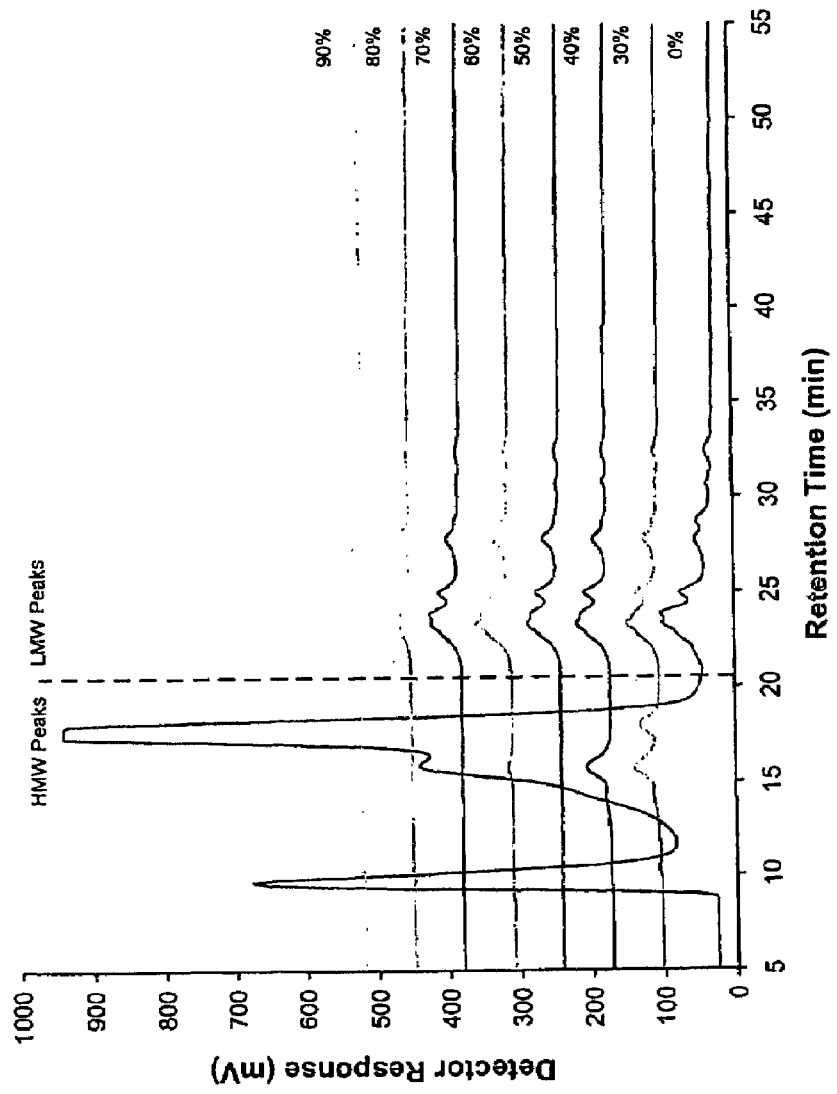
FIG. 11. Shows gel filtration chromatography profiles of deer blood LMW extracts prepared using the new in situ extraction process, and with varying concentrations of ethanol in the pre-treatment incubation step (gel filtration chromatography profiles of freeze-dried deer blood samples extracted with 0.05M phosphate buffer (pH 6.9) following pre-treatment for 3 hours with a 6:1 (v/w) ratio of 30%, 40%, 50%, 60%, 70%, 80%, or 90% ethanol, or without pre-treatment (0% ethanol))
Figure 12:
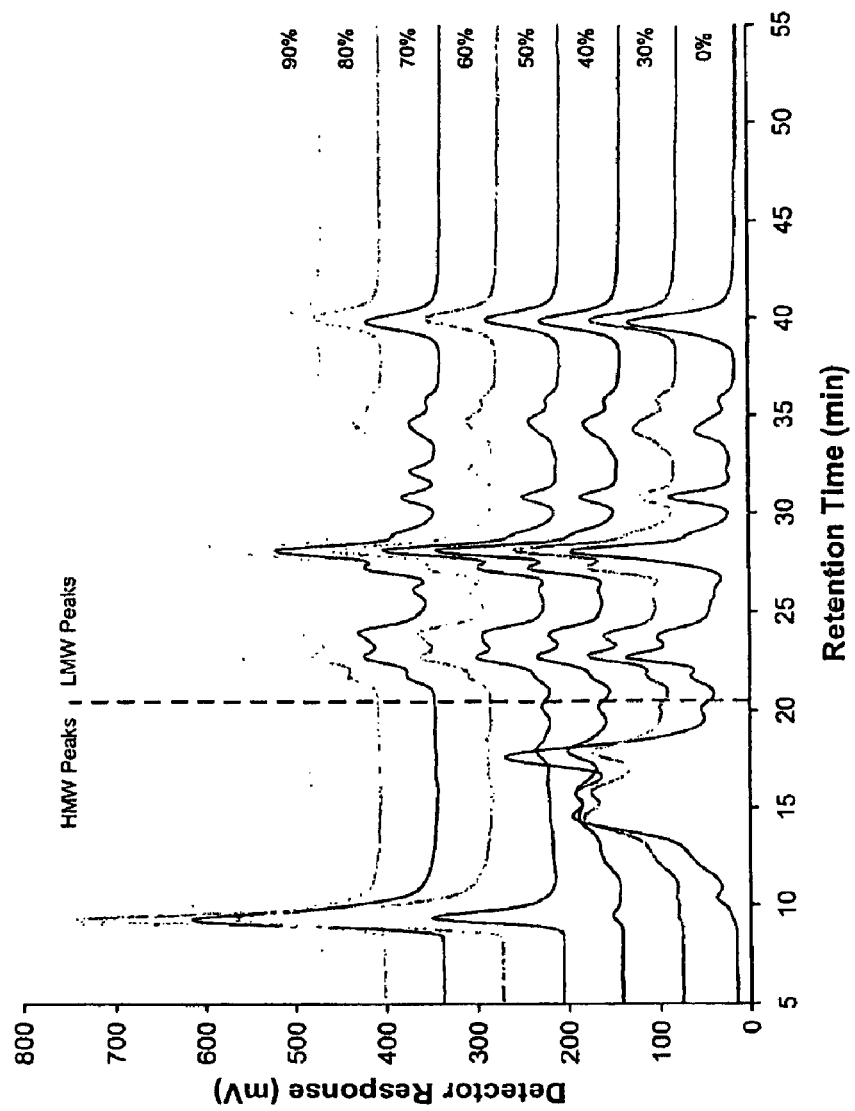
FIG. 12. Shows gel filtration chromatography profiles of sheep liver LMW extracts prepared using the new in situ extraction process, and with varying concentrations of ethanol in the pre-treatment incubation step (gel filtration chromatography profiles of freeze-dried sheep liver samples extracted with 0.05M phosphate buffer (pH 6.9) following pre-treatment for 3 hours with a 6:1 (v/w) ratio of 30%, 40%, 50%, 60%, 70%, 80%, or 90% ethanol, or without pre-treatment (0% ethanol))

The gel filtration chromatography profiles of freeze-dried deer placenta, freeze-dried deer blood and of freeze-dried sheep liver samples extracted with 0.05M phosphate buffer (pH 6.9) following pre-treatment for 3 hours with a 6:1 (v/w) ratio of 30%, 40%, 50%, 60%, 70%, 80% or 90% ethanol, or without pre-treatment, are shown in FIGS. 10, 11 and 12, respectively. These demonstrate that pre-treatments with a range of ethanol concentrations (especially 70% ethanol) are effective for reducing the proportion of high molecular weight proteins in aqueous extracts prepared from these materials, similar to freeze-dried deer velvet antler.

Figure 13:
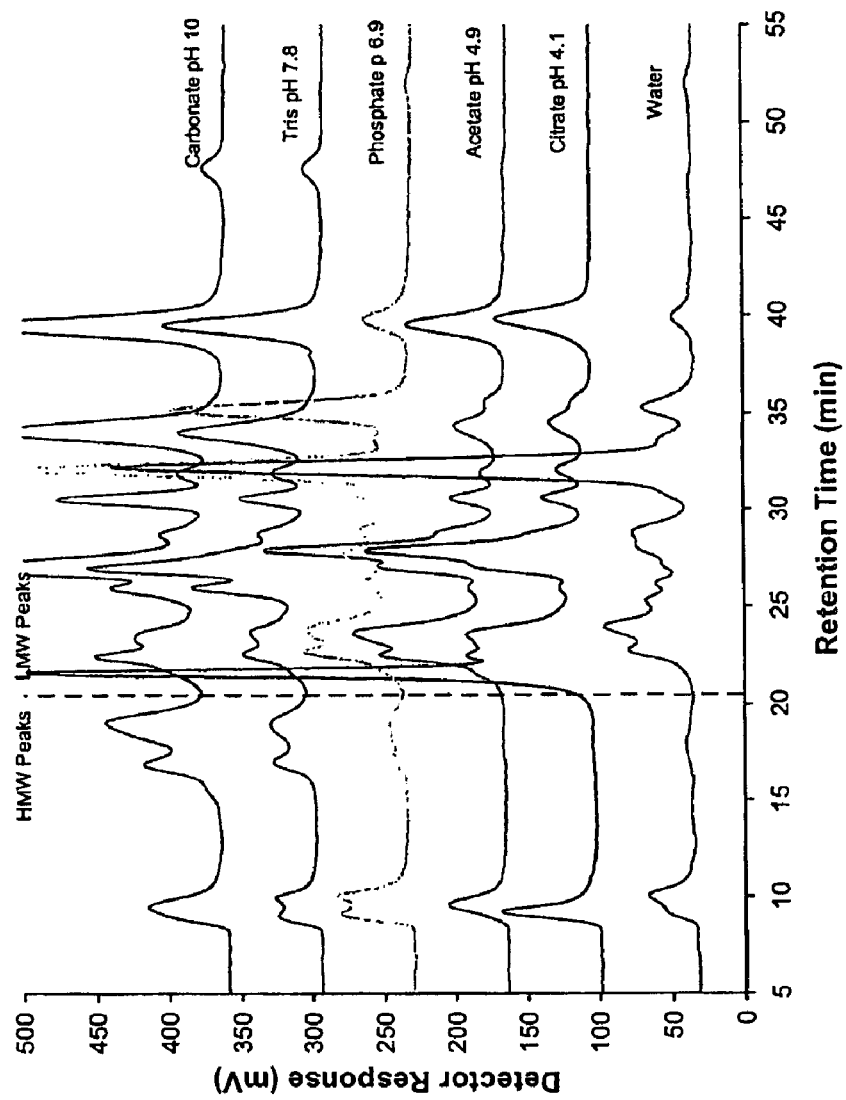
FIG. 13. Shows gel filtration chromatography profiles of sheep liver LMW extracts prepared using the new in situ extraction process, and with varying buffers used for the aqueous extraction step (gel filtration chromatography profiles of freeze-dried sheep liver samples extracted with various buffers (each 0.05M) or with water, following pre-treatment for 3 hours with a 6:1 (v/w) ratio of 70% ethanol)

The effect of the buffer used for the aqueous extraction of sheep liver following pre-treatment for 3 hours with a 6:1 (v/w) ratio of 70% ethanol is shown in FIG. 13. As for deer velvet, the extraction of high molecular proteins is least evident from sheep liver when the aqueous extraction is performed at acidic pH (using citrate or acetate buffers).

The new process is thus shown to be applicable to tissues and materials other than deer velvet.

Use of Frozen Deer Velvet Tissue in the New Process

Figure 14:
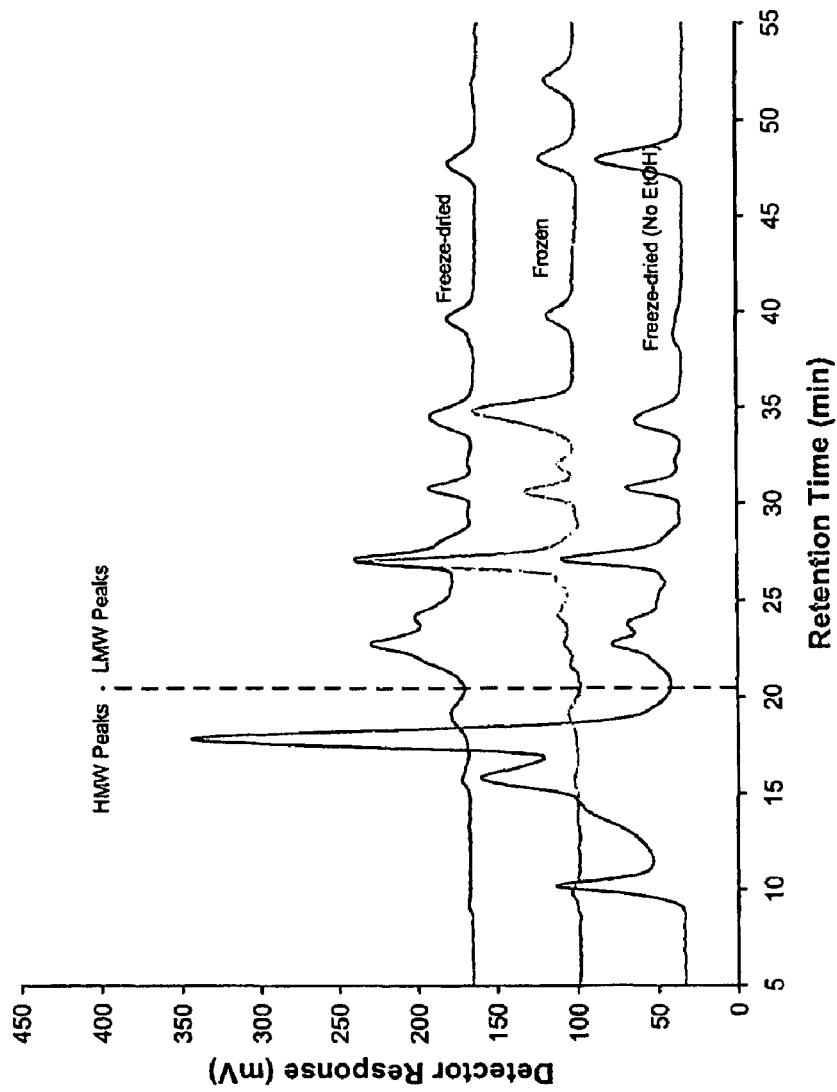
FIG. 14. Shows a gel filtration chromatography profile of a LMW extract prepared from frozen deer velvet tissue using the new in situ extraction process, compared with a similar extract prepared from freeze-dried deer velvet tissue (gel filtration chromatography profiles of frozen and of freeze-dried deer velvet samples extracted with 0.05M phosphate buffer (pH 6.9) following pre-treatment for 3 hours with a 6:1 (v/w) ratio of 70% ethanol, compared to a sample of freeze-dried deer velvet similarly extracted without ethanol pre-treatment).

FIG. 14 shows the gel filtration profile of a LMW extract prepared from a sample of minced frozen deer velvet tissue using the new extraction process, compared to that of a similar extract prepared from freeze-dried velvet. Essentially no high molecular weight proteins are evident in the protein profile of the extract from the frozen sample. This demonstrates that the new process significantly reduces the proportion of high molecular weight proteins in aqueous extracts derived from frozen tissue similar to that from dried tissue.

Discussion

We have shown that the molecular weight distribution of proteins in aqueous extracts prepared from tissue that has been pre-treated with an organic solvent (ethanol) is similar to that obtained following precipitation of high molecular weight proteins from aqueous solutions of standard total protein extracts by addition of the solvent in the cold.

The new process has been exemplified by the use of ethanol, acetonitrile, acetone, methanol, and propan-2-ol, but other solvents (including, but not limited to propan-1-ol, butan-1-ol) would reasonably be expected to be usable.

Key advantages of the new process relative to the liquid phase one are that it
 uses much less organic solvent;
 does not result in dilution of the tissue extract.

This reduces the hazards involved in the use of a flammable solvent and also reduces liquid handling problems. Furthermore the necessity for a separate clarification step to remove precipitated proteins is removed by the new process. Instead, the high molecular weight proteins are simply rendered insoluble in situ within the tissue. Subsequent extraction under aqueous conditions then results in solubilisation of only low molecular weight proteins and peptides.

A key reason for the preferred use of ethanol as the organic solvent in the new process is due to its anti-microbial activity (particularly at a concentration of 70%). This has the desirable effect of reducing the bacterial loading of the tissue raw material immediately prior to the aqueous extraction.

The high levels of IGF-1, IGF-2, TGFβ₁, TGFβ₂ and EGF-like activity in the LMW extracts of deer velvet show that growth factor activity is retained by the new extraction process. It is thus reasonable to expect that the level of other growth factors will also be enriched in extracts of tissues following the pre-treatment with ethanol.

The new process has been exemplified by the use of deer velvet, deer placenta, deer blood and sheep liver. Similarly it is reasonable to assume that proteins in tissues other than these can similarly be rendered insoluble by the ethanol pre-treatment process, to provide enrichment of the low molecular weight fractions in subsequent aqueous extracts.

The use of both dried and frozen deer velvet tissue in the new process has been exemplified. Similarly it is reasonable to assume that other tissues can be utilised in the new process in either a dried or a non-dried (i.e. frozen or fresh) state.

Aspects of the present invention have been described by way of example only and it should be appreciated that modifications and additions may be made thereto without departing from the scope thereof as defined in the appended claims.

REFERENCES

Scopes, R.K. (1987) "Protein Purification, Principles and Practice, 2$^{nd}$ Edition", *Springer Verlag*, New York, p 38.

Tani, H., Kamidate, T. and Watanabe, H. (1997) "Micelle-mediated extraction", *Journal of Chromatography A*, 780: 229-241.

Betzing, H. and Lekim, D. (1975) "Process of manufacturing enzyme preparation rich in lipase", Patent GB1454983.

What is claimed is:

1. A process for isolating native, low molecular weight ("LMW") peptides, which have a molecular weight, wherein said molecular weight is less than or equivalent to 10 kDa from tissue in situ comprising:
 a) homogenizing the tissue;
 b) mixing the homogenized tissue with an organic solvent to form a fully-wetted slurry;
 c) standing or agitating the slurry to denature high molecular weight proteins proteins in situ within the homogenized tissue;
 d) removing and discarding the organic solvent from the homogenized tissue prior to undertaking step (e);
 e) mixing the organic solvent-treated homogenized tissue of step d) that comprises the in situ-denatured high molecular weight proteins and the low molecular weight ("LMW") peptides, which have a molecular weight, wherein said molecular weight is less than or equivalent to 10 kDa with water or an aqueous, non-organic solution that consists essentially of water and aqueous salts and/or buffer solutions, and does not contain ethanol, to extract the low molecular weight ("LMW") peptides, which have a molecular weight, wherein said molecular weight is less than or equivalent to 10 kDa; and f) separating a liquid extract from the homogenized tissue residue of step e) to obtain an aqueous solution containing the low molecular weight peptide fraction removed from the tissue.

2. A process as claimed in claim 1 wherein prior to undertaking step a) the tissue is dried in a pre-step.

3. A process as claimed in claim 2 wherein the tissue is freeze dried.

4. A process as claimed in claim 1 wherein the organic solvent of step b) is ethanol.

5. A process as claimed in either claim 1 or claim 4 wherein the organic solvent in step b) is 70% ethanol.

6. A process as claimed in either claim 1 or claim 4 wherein the organic solvent in step b) is ethanol having a concentration of substantially between 50%-80% ethanol.

7. A process as claimed in either claim 1 or claim 4 wherein the organic solvent in step b) is ethanol having a concentration of substantially between 60%-70% ethanol.

8. A process as claimed in claim 1 wherein the organic solvent of step b) is absolute ethanol which is added to the homogenized tissue to provide a total water content of approximately 30% with respect to the volume of ethanol.

9. A process as claimed in claim 1 wherein at step c) the slurry is allowed to stand or is agitated for a period of at least substantially 1 hour.

10. A process as claimed in claim 1 wherein at step c) the slurry is left to stand or is agitated for a period of substantially 3 hours or more.

11. A process as claimed in either claim 9 or claim 10 wherein the slurry is left to stand or is agitated at a temperature in the range 10-30° C.

12. A process as claimed in claim 1 comprising additional step d1) wherein the solvent treated tissue of step d) is fully dried prior to undertaking step e).

13. A process as claimed in either claim 1 or claim 12 wherein the organic solvent-treated tissue of steps d) or d1) is mixed with water or aqueous solution for substantially 1 hour.

14. A process as claimed in claim 13 wherein the mixing is performed at an ambient temperature (as herein defined) or below.

15. A process as claimed in claim 1 comprising additional step g) wherein steps e) to f) are repeated one or more times, to improve the yield of liquid extract from the tissue residue of step e).

16. A process as claimed in either claim 1 or claim 15 wherein the liquid extract from steps f) or g) is dried to obtain a low molecular weight peptide extract.

* * * * *